United States Patent [19]
Seidel et al.

[11] Patent Number: 6,071,689
[45] Date of Patent: Jun. 6, 2000

[54] SYSTEM FOR IMPROVING YIELD OF SEXED EMBRYOS IN MAMMALS

[75] Inventors: George Seidel, LaPorte; Lisa Herickhoff; John Schenk, both of Fort Collins, all of Colo.

[73] Assignee: XY, Inc., Fort Collins, Colo.

[21] Appl. No.: 09/015,454

[22] Filed: Jan. 29, 1998

Related U.S. Application Data

[63] Continuation-in-part of application No. 09/001,394, Dec. 31, 1997.
[51] Int. Cl.[7] .......................... A61K 35/52; A61K 35/48; A61D 19/02; A61D 19/04; C12Q 1/68
[52] U.S. Cl. .................................... 435/2; 435/6; 435/7.1; 435/7.21; 435/325; 600/33; 600/34; 600/35; 800/8
[58] Field of Search ................................. 435/6, 7.1, 7.21, 435/7.2, 440, 325, 2; 800/2, 8; 600/33, 34, 35

[56] References Cited

U.S. PATENT DOCUMENTS 5,589,457  12/1996  Wiltbank .................................... 514/12

FOREIGN PATENT DOCUMENTS

WO 96/12171  10/1995  WIPO.

OTHER PUBLICATIONS

McKinnin, A. and Voss, J., "Equine Reproduction", Lea & Febiger, Philadelphia, 1993, pp 291, 299–302, 345–348, 739–797.

Blanchard, T. and Dickson, V., Stallion Management, The Veterinary Clinics of North America, Equine Practice, vol. 8, No. 1, Apr. 1992, pp 207–218.

Vazquez, J. et al., "Nonsurgical Uterotubal Insemination in the Mare", Proceedings of the 44th Annual Convention of the American Association of Equine Practitioners, Baltimore, Maryland, Dec. 6–9, 1998, vol. 44, pp 68–89.

Welch, G., et al., "Flow Cytometric Sperm Sorting and PCR to Confirm Separation of X– and Y– Chromosome Bearing Bovine Sperm", Animal Biotechnology, 6 (2), 131–139, 1995. pp 131–139.

Pinkel, D., et al., "Flow Cytometric Determination of the Proportions of X– and Y– Chromosome–Bearing Sperm in Samples of Purportedly Separated Bull Sperm", Journal of Animal Science, vol. 60, No. 5, 1985, pp 1303–1307.

Johnson, L.A., and Pinkel, D., "Modification of a Laser–Based flow Cytometer for High–Resolution DNA Analysis of Mammalian Spermatozoa", Cytometry 7, 1986, pp 268–273.

Pickett, B.W., and Shiner, K.A., "Recent developments in artificial insemination in horses", Livestock Production Science, 40, 1994, pp 31–36.

Meinert, C., et al., "Advancing the time of ovulation in the mare with a short–term inplant releasing the GnRH analogue deslorelin", Equine Veterinary Journal, 25, 1993, pp 65–68.

Rath, D., et al., "Production of Piglets Preselected for Sex Following in Vitro Fertilization with X and Y Chromosome–Bearing Spermatozoa Sorted by Flow Cytometry", Theriogenology, 47, 1997, pp 795–800.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, Apr. 1996, pp 127–130.

Johnson, L.A., et al., "Sex Preselection in Rabbits: Live Births from X and Y Sperm Separated by DNA and Cell Sorting", Execptional Paper–Rapid Publication, XP–002103476, Biology of Reproduction 41, 199–203, 1989. pp 199–203.

Nowshari, et al, Theriogenology 43:797–802 1995.

Karabinus et al. Journal of Dairy Science. 74:3836–3848, 1991.

Seidel et al. Theriogenology. 48: 1255–1264, 1997.

Catt et al. Reprod. Dom. Anim. 32: 251–258, 1997.

Johnson. Dtsch. tierarztl. Wschr. 103:288–291, 1996.

Nowshari et al. Theriogenology 43: 797–802, 1991.

*Primary Examiner*—Carla J. Myers
*Attorney, Agent, or Firm*—Santangelo Law Offices, P.C.

[57] ABSTRACT

Improved insemination systems particularly adapted to use for sex-selected sperm sorting include systems which achieve superovulation and then multiple embryo production with sexed embryos. These systems combine with other techniques, including techniques for enhanced sheath fluid and other strategies which minimize stress on the sperm cells, and, potentially, a 2.9 percent sodium citrate sheath solution for bovine species and a hepes bovine gamete media for equine species. Improved collection systems and techniques for the process are described so that commercial application of sperms samples as well as the resulting animals may be achieved.

20 Claims, 4 Drawing Sheets

SYSTEM FOR IMPROVING YIELD OF SEXED EMBRYOS IN MAMMALS

This is a continuation-in-part application of an application filed on Dec. 31, 1997, entitled: "Improved Sheath Fluids and Collection Systems for Sex-Specific Cytometer Sorting of Sperm" bearing Ser. No. 09/001,394.

BACKGROUND OF THE INVENTION

This invention relates generally to the field of sex selection in mammalian offspring. It is especially relevant to the aspect of low dose artificial insemination for creating the desired sex of offspring. Particularly, the invention relates to systems for sorting sperm via flow cytometry for sex-specific and low dose efforts at artificial insemination or the like.

For ages it has been desired to select the sex of specific offspring. Beyond obvious psychological aspects, the actual sex selection of mammalian offspring has significant economic consequences when one considers its application to food producing animals such as cattle as well as celebrated trophy animals such as horses and the like. This great desire has resulted in a significant variety of efforts to achieve sex-selected offspring. Probably the effort which has appeared most likely to achieve the desired results has been efforts at sorting and selecting between X and Y sperm prior to insemination.

One of the challenges that effort at sorting X and Y sperm has faced is the large numbers of sperm involved. In natural insemination sperm are produced in some species by the billions; in artificial insemination less, but still significantly large numbers of sperm are used. For instance, artificial insemination techniques commonly use ten million to five hundred million sperm (depending on species). Thus a significant number of sperm are necessary even in an artificial insemination environment.

Many methods have been attempted to achieve the separation of X- and Y-chromosome bearing sperm. These methods have ranged from magnetic techniques such as appears disclosed in U.S. Pat. No. 4,276,139 to columnar techniques as appears disclosed in U.S. Pat. No. 5,514,537 to gravimetric techniques as discussed in U.S. Pat. Nos. 3,894,529, reissue Pat. No. 32350, U.S. Pat. Nos. 4,092,229, 4,067,965, and 4,155,831. Electrical properties have also been attempted as shown in U.S. Pat. No. 4,083,957 as well as a combination of electrical and gravimetric properties as discussed in U.S. Pat. Nos. 4,225,405, 4,698,142, and 4,749,458. Motility efforts have also been attempted as shown in U.S. Pat. Nos. 4,009,260 and 4,339,434. Chemical techniques such as those shown in U.S. Pat. Nos. 4,511,661 and 4,999,283 (involving monoclonal antibodies) and U.S. Pat. Nos. 5,021,244, 5,346,990, 5,439,362, and 5,660,997 (involving membrane proteins), and U.S. Pat. Nos. 3,687,803, 4,191,749, 4,448,767, and 4,680,258 (involving antibodies) as well as the addition of serum components as shown in U.S. Pat. No. 4,085,205. While each of these techniques has been presented as if to be highly efficient, in fact at present none of those techniques yield the desired level of sex preselection.

At present, the only quantitative technique used to achieve the separation of X-and Y-chromosome bearing sperm has been that involving individual discrimination and separation of the sperm through the techniques of flow cytometry. This technique appeared possible as a result of advances and discoveries involving the differential dye absorption of X-and Y- chromosome bearing sperm. This was discussed early in U.S. Pat. No. 4,362,246 and significantly expanded upon through the techniques disclosed by Lawrence Johnson in U.S. Pat. No. 5,135,759. The Johnson technique of utilizing flow cytometry to separate X- and Y-chromosome bearing sperm has been so significant an advancement that it has for the first time made the commercial separation of such sperm feasible. While still experimental, separation has been significantly enhanced through the utilization of high speed flow cytometers such as the MoFlo® flow cytometer produced by Cytomation, Inc. and discussed in a variety of other patents including U.S. Pat. Nos. 5,150,313, 5,602,039, 5,602,349, and 5,643,796 as well as international PCT patent publication WO 96/12171. While the utilization of Cytomation's MoFlo® cytometers has permitted great increases in speed, and while these speed increases are particularly relevant given the high number of sperm often used, certain problems have still remained. In spite of the almost ten-fold advances in speed possible by the MoFlo® flow cytometer, shorter and shorter sorting times have been desired for several reasons. First, it has been discovered that as a practical matter, the sperm are time-critical cells. They loose their effectiveness the longer they remain unused. Second, the collection, sorting, and insemination timings has made speed an item of high commercial importance. Thus, the time critical nature of the sperm cells and the process has made speed an essential element in achieving high efficacy and success rates.

Other problems also exist ranging from the practical to the theoretical. On the practical side, it has been desired to achieve sex-sorted sperm samples using inexpensive disposable components and substances. Also on the expense side, it has been desired to be able to achieve sorting (as well as collection and insemination) in as efficient a labor event as possible. Thus, for commercial production and success in this field, improvements which might only represent an increase in efficiency may still be significant. Related to the practical aspect of expense, is the practical aspect of the delicateness and sensitivity of the entire process. In this regard, it has been desired to simplify the process and make it as procedurally robust as possible so that operator error or skill can play an ever decreasing role.

In addition to the delicateness of the process, it has always been known that the sperm themselves are extremely delicate cells. While this factor at first glance seems like it might be considered easily understood, in fact, the full extent of the cells' sensitivities have not yet been fully explored. In the context of flow cytometry in general, most sorted cells or particles have often been spherical or otherwise physically able to withstand a variety of abuses. This is not the case for sperm cells. In fact, as the present invention discloses, the processing through normal flow cytometer techniques may, in fact, be unacceptable for cytometric sorting of sperm cells in certain applications. The sensitivities range from dilution problems and the flow cytometer's inherent need to isolate and distinguish each cell individually as well as the pressure and other stresses which typical flow cytometry has, prior to the present invention, imposed upon the cells or other substances that it was sorting. This may also represent a unique factor for sperm cells because it appears that even though the sperm cell may appear to pass through the flow cytometer and be sorted with no visually discernable side-effects, in fact, the cells themselves may have been stressed to the point that they perform less than optimally in the insemination process. Thus, an interplay of factors seems involved and has raised unusual problems from the perspective of sperm cell sorting and ultimate use for artificial insemination.

Another problem which has remained—in spite of the great advances achieved through the Johnson patent and related technology—is the fact that prior to the present invention it has been extremely difficult to achieve lower dosage insemination with sexed sperm. While historically, some achievement of low dose insemination has occurred, it has appeared to be more on a theoretical or laboratory environment rather than from environments which are likely to be experienced in or applicable to a commercial application. In this regard, the desire has not been merely to achieve low dose insemination but rather to achieve low dose insemination with pregnancy success rates which are comparable to existing unsexed, high dosage artificial insemination efforts. Thus, the advances achieved by the present inventors in both sexed and low dose artificial insemination represent significant advances which may, for the first time, make commercial applications feasible.

Another problem which has been faced by those in the industry—again, in spite of the great advances by the Johnson patent and related technology—is the fact that the problem itself, namely, artificial insemination with a high success rate is one of a statistical nature in which a multitude of factors seem to interplay. Thus, the solutions proposed may to some degree involve a combination of factors which, when thoroughly statistically studied, will be shown to be necessary either in isolation or in combination with other factors. Such a determination is further compounded by the fact that the results themselves vary by species and may be difficult to ascertain due to the fact that testing and statistical sampling on a large enough data base is not likely to be worth the effort at the initial stages. For these reasons the invention can also involve a combination of factors which may, individually or in combination, represent the appropriate solutions for a given application. This disclosure is thus to be considered broad enough so that the various combinations and permeations of the techniques disclosed may be achieved. Undiscovered synergies may exist with other factors. Such factors may range from factors within the sorting or flow cytometer steps to those in the collection as well as insemination steps. At present, studies have been primarily achieved on bovine species, however, it is not believed that these techniques will be limited to such species or, for that matter to only sperm cells. It appears that the techniques used may have application beyond just sperm cells into areas which involve either sensitive items to be sorted or merely minimization of the impacts of the stresses of flow cytometry upon the item sorted.

Interestingly, while the present invention takes an approach to minimize the impacts and stresses upon the sperm cells, others appear to have actually taken steps away from this direction by increasing pressures and demands for speed and other such performance. Essentially, the drive for low dose insemination and high speed processing may, in an individual or perhaps interrelated fashion have posed problems which limited one another. Thus, while there has been a long felt but unsatisfied need for high speed, low dose sexed insemination, and while the implementing arts and elements have long been available, prior to the present invention the advances or perhaps combinations of advances had apparently been overlooked by those skilled in the art. Perhaps to some degree they failed to appreciate that the problem involved an interplay of factors as well as peculiar necessities for the types of cells (sperm cells or perhaps species-specific sperm cells) involved in this field. Interestingly, as the listing of efforts earlier in this discussion shows, substantial attempts had been made but they apparently failed to understand the problem inherent in such an area as low dose, sexed insemination and had perhaps assumed that because the natural service event involves perhaps billions of sperm, there may have been physical limitations to the achievement of artificial insemination with numbers which are as many as four orders of magnitude less in number. Thus, it may not be surprising that there was to some extent an actual teaching away from the technical direction in which the present inventors went. Perhaps the results may even be considered unexpected to a degree because they have shown that sexed, low dose artificial insemination can be achieved with success rates comparable to those of unsexed, high dose artificial insemination. It might even be surprising to some that the techniques and advances of the present invention in fact combine to achieve the great results shown. While each technique could, in isolation, be viewed by some as unremarkable, in fact, the subtle changes appear to afford significant advances in the end result—whether considered alone or in combination with other subtle changes.

Thus, until the present invention the achievement of success rates for low dose, sexed artificial insemination has not been possible with levels of performance necessary or simplified procedures likely to be necessary to achieve commercial implementation. The present invention discloses techniques which permit the achievement of improved performances and thus facilitate the end result desired, namely, low dose, sexed artificial insemination on a commercial basis.

SUMMARY OF THE INVENTION

Accordingly, the present invention provides improved sheath and collector systems for sorting of sperm cells to determine their sex through a flow cytometer. The sheath fluid as typically used in a flow cytometer is replaced with a fluid which minimizes the stress on the sperm cells as they are sorted. Furthermore, the collection system is improved to minimize both the physical and chemical stress to which the sperm cells are subjected. Various techniques and substances are represented but as those skilled in the art will readily understand, various combinations and permutations can be used in the manner which may be optimized for performance based in the species, goals and other parameters involved in a specific processing application.

An object of the invention is thus to achieve better sorting for substances such as sperm cells. A goal is to minimize the impact the sorting function itself has on the cells or other sensitive items which may be sorted. A particular goal is to minimize the impact the sheath fluid imposes upon the cells and to potentially provide a sheath fluid which affirmatively acts to assist the cells in handling the various stresses involved. A parallel goal is to provide substances and techniques which are especially suited for sperm cells in general, for bovine sperm cells, for equine sperm cells, and for the separation of such sperm cells into X- and Y-chromosome bearing components. Similarly a goal is to minimize the impacts that the collection phase (e.g., after sorting) has upon the cells and to minimize the physical impact as well as chemical impacts on such sex sorted sperm cells. Thus a goal is to achieve as unaffected a sorted result as possible.

Another object of the invention is to achieve low dose, sorted insemination on levels and with success rates which are comparable to those of the typical unsexed, high dose artificial insemination. Thus the prior goals of minimizing the stress or potential damage upon the sperm cells is important. Sorting in a manner which affords both high speed and low stress sorting, and which is especially adapted for sperm cell sorting in a low dose context is an important goal as well. The goals of providing sheath and other fluids which do not negatively affect the fertility of the sperm and which are compatible with artificial insemination are also important.

Naturally further objects of the invention are disclosed throughout other areas of the specification and claims.

DETAILED DESCRIPTION OF THE PREFERRED EMBODIMENT

As will be seen, the basic concepts of the present invention can be combined and embodied in a variety of ways. The invention involves both improved flow cytometer systems as well as systems for the creation of sex-specific sperm samples which may be used in artificial insemination and the animals produced by such techniques. Furthermore, the techniques are disclosed in a general fashion so that they may be applied to specific systems and applications once the general principals are understood. While device enhancements are disclosed it should be understood that these enhancements not only accomplish certain methods but also can be varied and combined in a number of ways. Importantly, as to all of the foregoing, each of these facets should be understood to be encompassed by this disclosure.

As mentioned, the basic goal is that of separating the X-bearing sperm from the Y-bearing sperm. This is done in a manner which isolates the two types of sperm so that each can be separately packaged and dealt with. The isolation is preferably done through the use of flow cytometry. Flow cytometry in general is a technique which is well understood. For instance, the basic aspects of it are shown and discussed in a variety of patents to Cytomation, Inc. such as the U.S. Patents and other publications listed earlier. Each of these patents and the references cited therein, are incorporated by reference, thus those skilled in the art can easily understand the basic principles involved.

Figure 1:
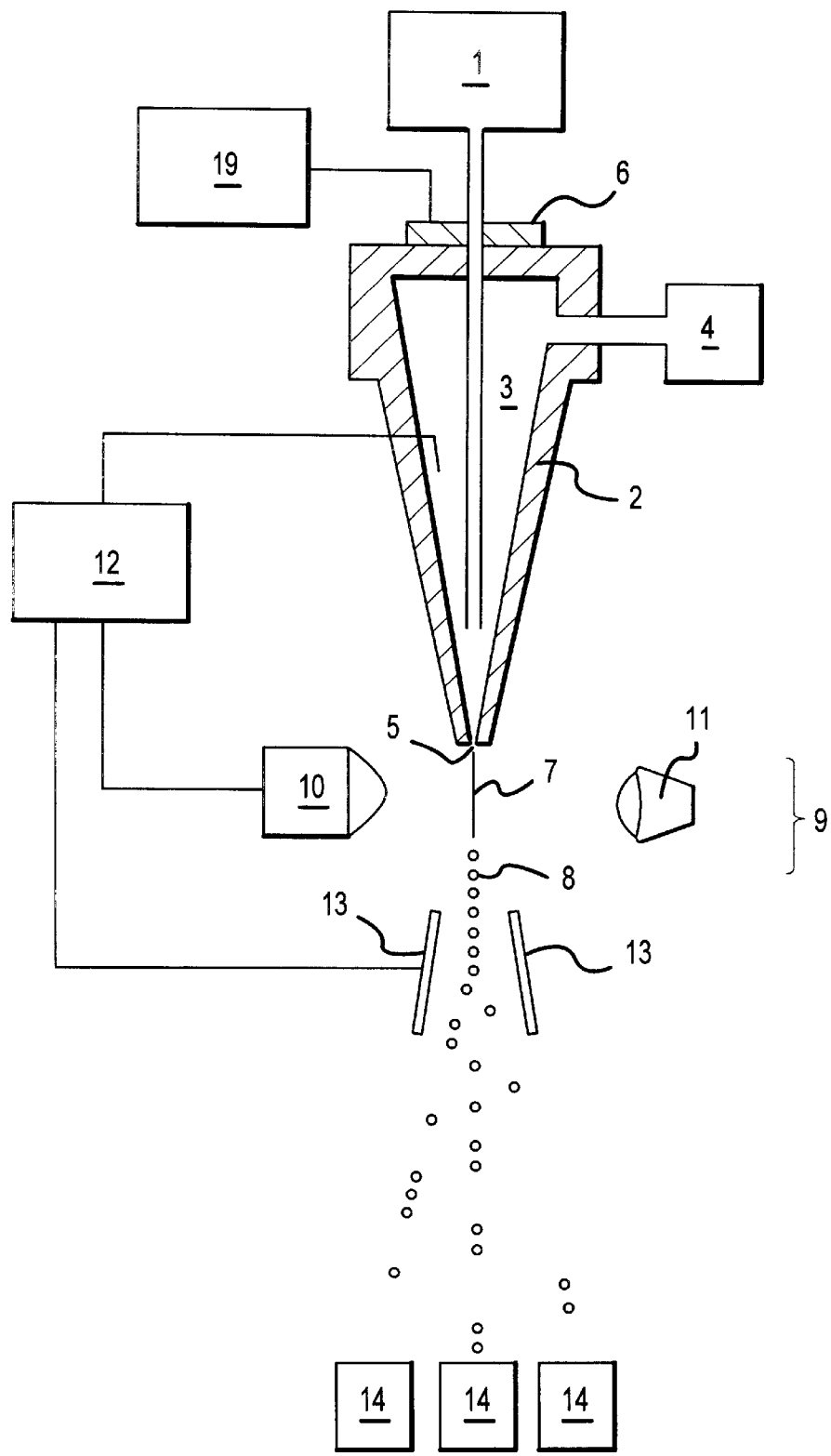
FIG. 1 is a schematic diagram of a sorter system according to the present invention.

Essentially, flow cytometry involves sorting items, such as cells, which are provided to the flow cytometer instrument through some type of cell source. A conceptual instrument is shown in FIG. 1. The flow cytometer instrument includes a cell source (1) which acts to establish or supply cells or some other type of item to be analyzed by the flow cytometer. The cells are deposited within a nozzle (2) in a manner such that the cells are surrounded by a sheath fluid (3). The sheath fluid (3) is usually supplied by some sheath fluid source (4) so that as the cell source (1) supplies its cells, the sheath fluid (3) is concurrently fed through the nozzle (2). In this manner it can be easily understood how the sheath fluid (3) forms a sheath fluid environment for the cells. Since the various fluids are provided to the flow cytometer at some pressure, they flow out of nozzle (2) and exit at the nozzle orifice (5). By providing some type of oscillator (6) which may be very precisely controlled through an oscillator control (19), pressure waves may be established within the nozzle (2) and transmitted to the fluids exiting the nozzle (2) at nozzle orifice (5). Since the oscillator (6) thus acts upon the sheath fluid (3), the stream (7) exiting the nozzle orifice (5) eventually and regularly forms drops (8). Because the cells are surrounded by a sheath fluid environment, the drops (8) may contain within them individually isolated (generally) cells or other items.

Since the drops (8) generally contain isolated cells, the flow cytometer can distinguish and separate droplets based upon whether or not the appropriate cell or cells is/are contained within the drop. This is accomplished through a cell sensing system (9). The cell sensing system involves at least some type of sensor (10) which responds to the cells contained within each drop (8) as discussed at length in the seminal work (no pun intended) by Larry Johnson, namely, U.S. Pat. No. 5,135,759. As the Johnson patent explains for sperm cells, the cell sensing system (9) may cause an action depending upon the relative presence or relative absence of a particular dye which may be excited by some stimulant such as the laser exciter (11). While each type of sperm cell is stained by the dye, the differing length of the X-chromosome and the Y-chromosome causes different levels of staining, Thus, by sensing the degree of dye present in the sperm cells it is possible to discriminate between X-bearing sperm and Y-bearing sperm by their differing emission levels.

In order to achieve the ultimate separation and isolation of the appropriate cells, the signals received by sensor (10) are fed to some type of sorter discrimination system (12) which very rapidly makes the decision and can differentially charge each drop (8) based upon whether it has decided that the desired cell does or does not exist within that drop (8). In this manner the sorter discrimination system (12) acts to permit the electrostatic deflection plates (13) to deflect drops (8) based on whether or not they contain the appropriate cell or other item. As a result, the flow cytometer acts to sort the cells by causing them to land in one or more collectors (14). Thus by sensing some property of the cells or other items the flow cytometer can discriminate between cells based on a particular characteristic and place them in the appropriate collector (14). In the system presently used to sort sperm, the X-bearing sperm droplets are charged positively and thus deflect in one direction, the Y-bearing sperm droplets are charged negatively and thus deflect the other way, and the wasted stream (that is unsortable cells) is uncharged and thus is collected in an undeflected stream into a suction tube or the like.

Figure 2:
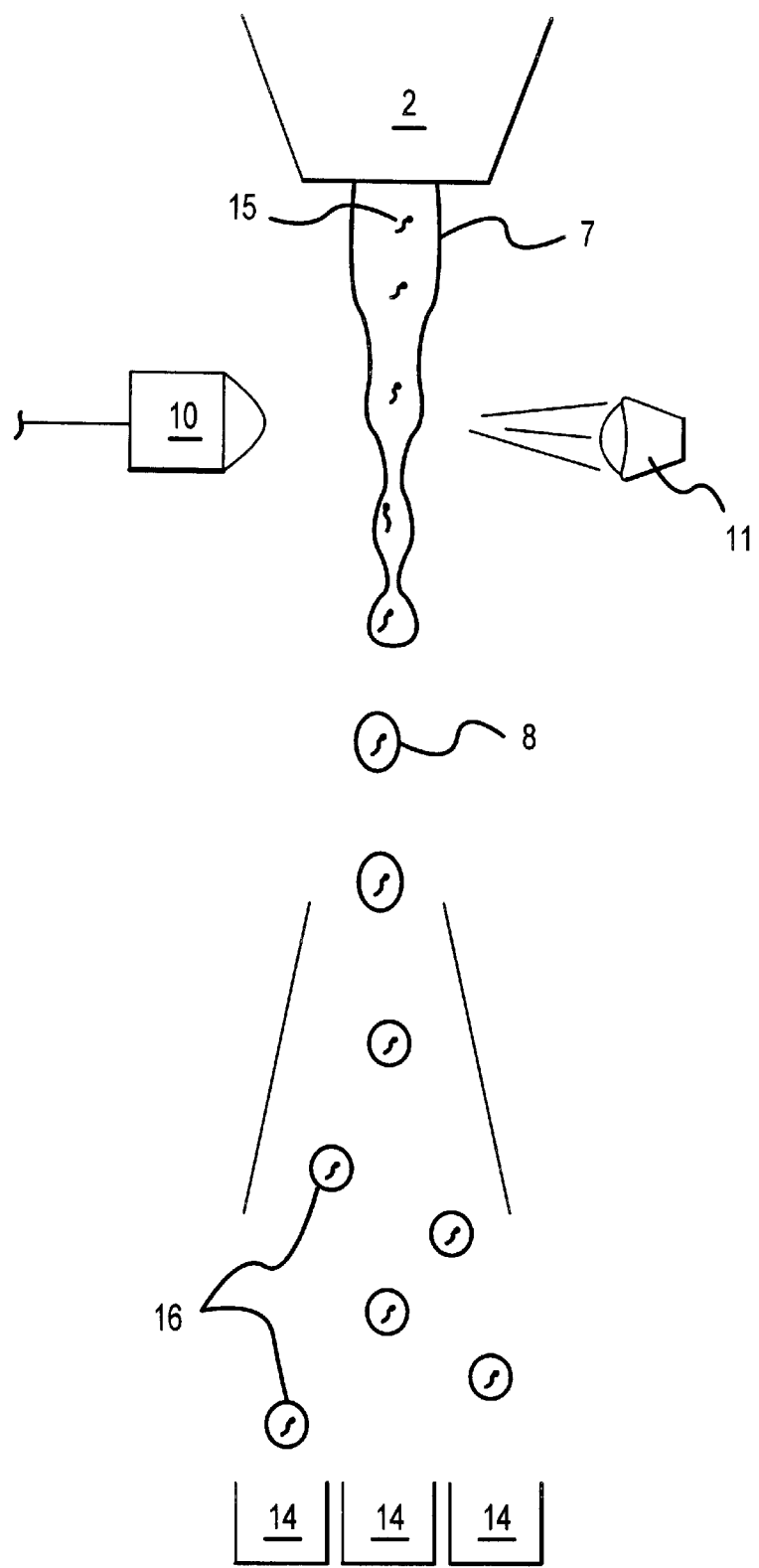
FIG. 2 is a diagram of the entrained cells in the free fall area of a typical flow cytometer.

Referring to FIG. 2, the process can be even further understood. As shown in that figure, the nozzle (2) emits a stream (7) which because of the oscillator (6) (not shown in FIG. 2) forms drops (8). Since the cell source (1) (not shown in FIG. 2) may supply sperm cells (15) which have been stained according to the Johnson technique, the light stimulation by laser exciter (11) is differentially determined by sensor (10) so that the existence or nonexistence of a charge on each drop (8) as it separates from stream (7) can be controlled by the flow cytometer. This control results in positively charged, negatively charged, and uncharged drops (8) based upon their content. As shown in FIG. 2, certain drops are shown as deflected drops (16). These deflected drops (16) are those containing sperm cells (15) of the one or the other sex. They are then deposited in the appropriate collector (14) for later use.

One of the aspects of flow cytometry which is particularly important to its application for sperm sorting is the high speed operation of a flow cytometer. Advances have been particularly made by the flow cytometers available through Cytomation, Inc. under the MoFlo® trademark. These flow cytometers have increased sorting speeds extraordinarily and have thus made flow cytometry a technique which is likely to make feasible the commercial application of sperm sorting (among other commercial applications). They act to achieve high speed sorting, that is at a speed which is notably higher than those otherwise utilized. Specifically, Cytomation's MoFlo® flow cytometers act with oscillator frequencies of greater than about five kilohertz and more specifically can be operated in the 10 to 30 or even the 50 kilohertz ranges. Thus droplets are formed at very high frequencies and the cells contained within the sheath fluid environment can be emitted very rapidly from the nozzle (2). As a result, each of the components such as the nozzle (2) oscillator (6), and the like which make up and are part of a flow cytometer system result in a high speed cell sorter. In the application of a high speed cell sorter to the sorting of sperm cells, sorting at rates of greater than about 500 sorts per second is achieved. In fact, rates of sorting in the thousand and twelve hundred ranges have already been achieved through a high speed cell sorter. Importantly, it should be understood that the term "high speed" is a relative term such that as other advances in flow cytometry and specific applications are achieved, the aspect which is considered "high" may be varied or may remain absolute. In either definition, the general principle is that the sorting may occur at rates at which the parameters and physical characteristics of the flow cytometer are significant to the cells themselves when sorting particular cells such as sperm cells.

One aspect of high speed sorting which appears to come into play when sorting sperm cells is that of the pressures and other stresses to which the sperm cells are subjected within the flow cytometer. For instance, when operating at high speeds (and an alternative definition of "high speed"), flow cytometers can be operated at a pressure of 50 pounds per square inch and even 60 and higher pounds per square inch. These pressures may be considered high because they may result in effects upon the cells being sorted. The key as disclosed in the present invention for this facet is the fact that the stress thresholds of the particular cells are the determining factor. Additionally as further knowledge is gained it may be shown that the stress thresholds are a function of combined effects such as the particular species or the particular prior or subsequent handling of the cells. The key in this regard is that the stress imposed upon the cells can, in fact, alter their viability and their ability to achieve the desired result. In the pressure case, it may be that merely subjecting the sperm cells to a higher pressure as a result of the operation of the flow cytometer at that pressure may result in decreased performance of the cells. The present invention in one regard acts to minimize these stresses and thus results in greater efficacies as well as lower dosages as discussed later.

In considering the stress aspect of the cells, the present invention acts in a fashion which minimizes the stresses. These stresses can be minimized at any point in the over all cycle or process of collecting, sorting or even inseminating the animal. Importantly, the stress imposed by the handling of the cells within the flow cytometer appears significant for this application. In one embodiment of the invention, the sheath fluid is specifically selected so that it can serve in a coordinated fashion with both (or either) the pre-sort cell fluid environment or the post-sort cell fluid environment. While naturally it is possible to adjust either the pre- or post-sort fluids, in one embodiment the invention adjusts the sheath fluid (3) so that it imposes significantly less stress upon the cells than was previously accomplished. In one regard the invention is remarkable in that it removes the total focus from that of operation of the flow cytometer to a focus on handling and removing stress from the cells themselves. For instance, while it has been known to utilize fluids having a proper pH factor or osmoality, the present invention recognizes that there may be certain chemical compositions to which the cells may be hyper-responsive. These hyper-responsive chemical compositions may naturally vary based upon the cells or even the prior handling of the cells. Importantly at present it appears that for sperm cells certain metabolic chemical compositions such as citrate seem to prevent unusually high stresses upon the cells. Thus, the hyper-responsive chemical compositions can be defined as those to which the cells are particularly responsive in the context of their functionality and the then-existing handling techniques. As to sperm cells it appears that metabolic compositions, specifically citrate constancy for bovine sperm cells and hepes buffer constancy for equine sperm cells may be very important. Thus the present invention acts to minimize the changes through the type of operation or the selection of substances which may act as a means for minimizing the changes which the cells experience.

Figure 3:
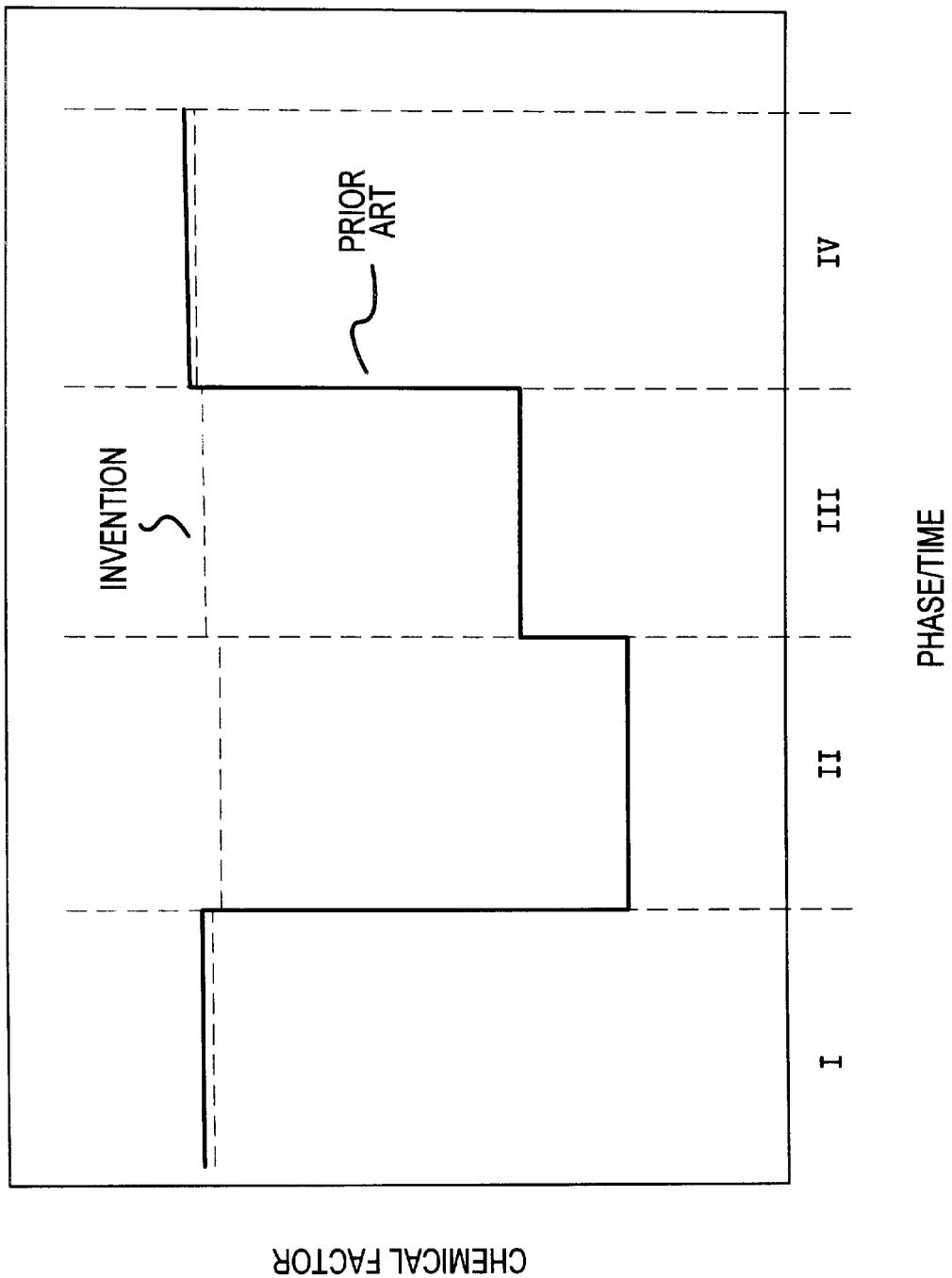
FIG. 3 is a conceptual diagram showing differences as they roughly appear as a result of the present invention.

For the sheath fluid, a substance is selected according to one embodiment of the invention so that it may be chemically coordinated to prevent minimal changes. Thus, by selecting the appropriate sheath fluid not only in context of flow cytometry parameters, but rather also in context of the cell parameters themselves, the changes experienced by the cells and the over all result of the sorting can be enhanced. This is shown conceptually in FIG. 3. FIG. 3 shows some type of chemical factor (such as citrate or other factors) as it may exist throughout the various phases of the process. For instance, the four phases shown might represent the following: phase I may represent the existence of the cells within the cell source (1), phase II might show the existence of the cells as they are sorted in the sheath fluid environment, phase III might show the cells as they are collected after sorting and phase IV might show the reconstituted cells in a storage medium after sorting. These four phases as shown for the prior art may experience vastly different chemical factor environments. As shown conceptually, however, in the present invention the cells may experience very little change, most notably the dip or drop experienced between phases I and II may be virtually absent. This is as a result of the selection of the appropriate sheath fluid as mentioned above. Thus, as a result of being subjected to an appropriate sheath fluid, the cells in the present invention may experience a much lower level of stress.

One of the potential generalities that may exist with respect to this phenomenon is the fact that certain chemical compositions may represent more hyper-responsive chemical compositions than others. While naturally this may vary based upon the species of sperm, the handling, or even the type of cell involved, it appears that the viability of the cells for their intended purpose (here, artificial insemination) varies greatly, naturally or because of sorting or both, and so the cells exhibit a hyper-responsive character with respect to that chemical composition. By selecting certain metabolic chemical compositions, most notably citrates or chemicals which are within the citric acid cycle, great advances appear possible. Thus for the bovine sperm application, the sheath fluid (3) is selected and coordinated so that it presents about a 2.9 percent sodium citrate composition. Specifically, the 2.9 percent sodium citrate solution may be created as follows:

1. Place 29.0 grams of sodium citrate dihydrate (Na$_3$C$_6$H$_5$O$_7$.2H$_2$O) in a 1,000 ml volumetric flask
   a. Dissolve sodium citrate in 3/4 of water batch, then add water to volume.
2. Add deionized or Nanopure water to make 1,000 ml final volume.
3. Transfer to bottles and autoclave at 15 lbs pressure (245° F.) for at least 30 minutes
   a. Autoclave solution using conditions to minimize evaporation (loose cover)
   b. Be careful that water does not boil away.
4. Cool slowly at room temperature.
5. Store sealed in a 5° C. cold room.
Further, for a sheath fluid, the sodium citrate solution may be filtered.
6. Filter with a .22 micron filter using aseptic techniques.

Interestingly, for equine sperm cells such a composition does not perform as well. Rather, it has been discovered that for equine sperm cells, a hepes buffered medium such as a hepes bovine gamete medium—particularly HBGM3 as previously created by J. J. Parrish for a bovine application—works well. This medium is discussed in the article "Capacitation of Bovine Sperm by Heparin", 38 Biology of Reproduction 1171 (1988) hereby incorporated by reference. Not only is this surprising because it is not the same type of substance as is utilized for bovine sperm, but the actual buffer, originally was developed for a bovine application. Thus in the equine application the sheath fluid is selected which contains the hepes buffer. This solution may have a pH at room temperature of about 7.54 (pH at 39° C.=7.4) with the following composition:

| Chemical | Dry weight (g/500 ml) |
|---|---|
| CaCl$_2$ | 0.145 |
| KCl$_2$ | 0.115 |
| MgCl$_2$.6H$_2$O | 0.004 |
| NaH$_2$PO$_4$.H$_2$O | 0.018 |
| NaCl | 2.525 |
| NaPyruvate | 0.011 |
| Lactic Acid (60%) | 1.84 ml |
| HEPES | 4.765 |
| NaHCO$_3$ | 0.420 |
| BSA (fraction V) | 3.0 |

One other aspect which may interplay in the present invention is the fact that the cells involved may experience unusual sensitivities. In one regard this may be due to the fact that sperm cells are in a class of cells which are non-repairing cells. That is, they do not have the ability to repair themselves and hence, they may need to be treated much more sensitively than is typical for flow cytometers or other handling equipment. Thus, it may be appropriate that the enhancement is particularly applicable when the flow cytometer acts to establish a source of sperm cells. Another potentially related aspect which may be unique to a class of cells such as sperm cells is the fact that their DNA is non-repairing, non-replicating, and non-transcribing. Either of these factors may come into play and so they may be relevant either individually or together. Thus, it may be that the teachings of the present invention apply to all gamete cells or even to viruses and the like which are non-repairing, non-translating, non-transcribing cells.

Figure 4:
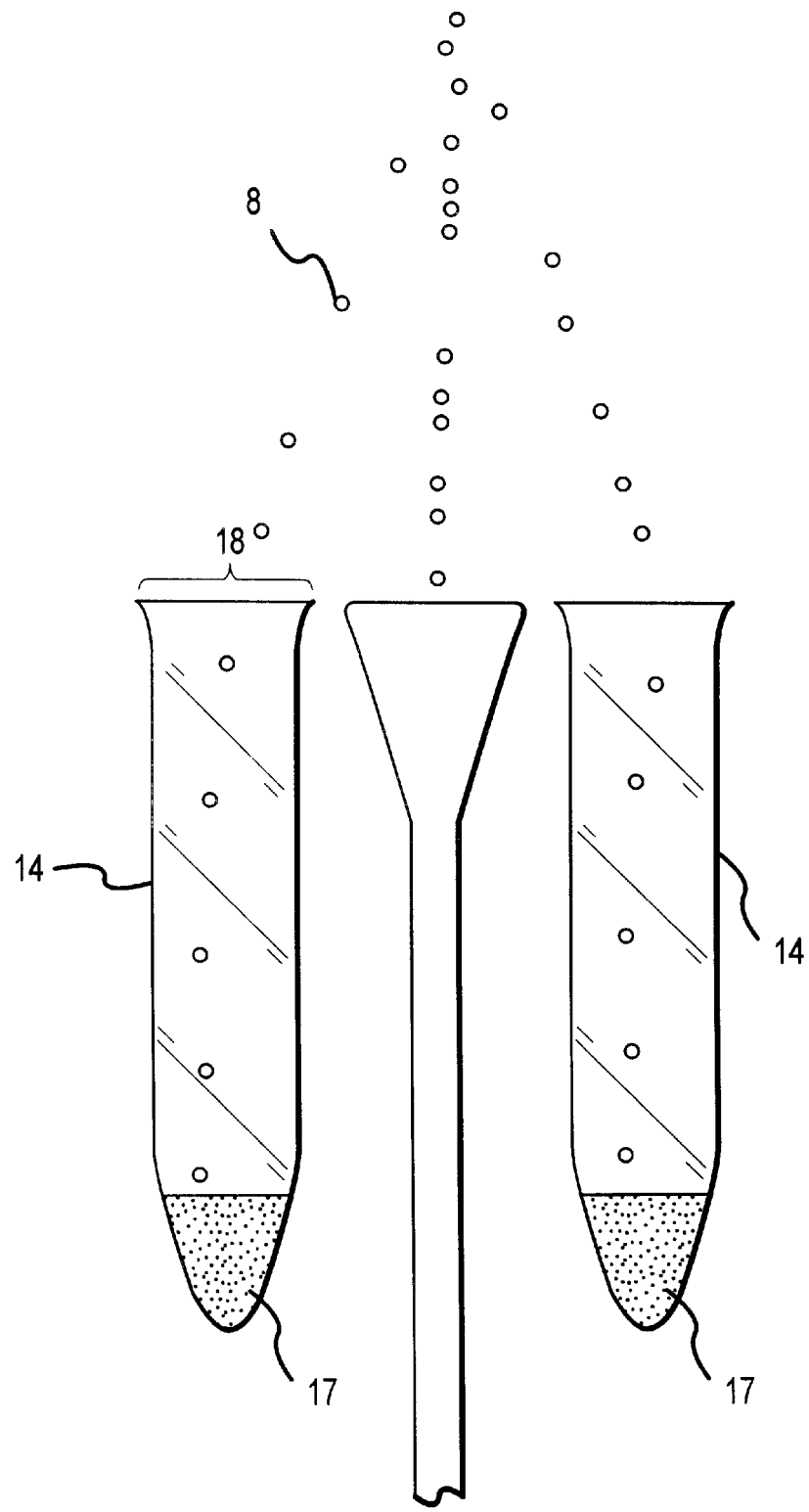
FIG. 4 is a diagram of the sorted cell stream as they are collected in the landing zone area.

A separate aspect of the flow cytometer processing which may also be important is the fact of properly treating the cells both chemically and physically after they are sorted. As shown in FIG. 4, as the cells within drops (8) land in collector (14), it may be important that the container which makes up the collector be properly sized so that it acts as some means of avoiding an impact between the cells and the container itself. While it has been known to place an initial collector fluid (17) in the bottom of the container to collect the cells so that they do not hit the bottom of the container, it appears that a simple widening of the container to address variations in stream presentation as well as the inevitable splashing due to the impact of the cells into the container can be used to enhance the result. In one regard this can act as a cushioning element so that cells which may be mechanically delicate, that is, they may break or be damaged by an impact can be treated appropriately. Thus when the cytometer source establishes cells which are physically delicate cells as the cells to be sorted, it may be important to provide some type of cushioning element such as a wide collection tube for which the opening width (18) serves to position the walls of the container in a manner which avoids contact with the cells. Thus the tube does not present side walls so close that there is any significant probability of contact between those cells being sorted and the walls of the tube. In this manner, in addition to the collector fluid (17), it may be desirable to include a wide collection tube as well. Perhaps merely providing a wide opening to the container which serves as part of the collector (14) may be sufficient. For applications utilizing high speed sorting of sperm cells, it has been found that providing a container having an inner diameter opening of at least 15 millimeters is believed to be sufficient. Specifically when utilizing a 14 ml Falcon test tube in such an application, minimal physical damage to the cells as a result of the collector (14) has been discovered.

It should be noted that even the 14 ml Falcon test tube may not be optimum. Specifically, it is believed that designing a collection container which matches the geometry of the stream (that is, a "stream-matched container") may be most optimal. This stream-matched container may have any or all of the following characteristics: a relatively wide orifice, an elliptically shaped orifice, a lesser height to width ratio than currently involved, an angled or otherwise coordinated presentation such as may present side walls which are parallel to the falling streams, and the like. It may also be desirable to provide a mounting element such as a movable element or medium like ball bearings or the like to permit variable orientation of the tube to match the falling stream desired to be collected. In addition, the physical characteristics for the class of containers such as the existing tube (described as a "Falcon-type" test tube) may include not only the width of the tube but also the material (such polystyrene to which the cells do not stick) out of which it is made and the like. (These material options are well known for the 14 ml Falcon tube.) Thus the container and it collection fluid may also serve as a cushioning element to minimize physical damage to the cells. It also can serve, by its size, to facilitate collection of adequate numbers of sperm without a significant dilution effect.

Another aspect of the collector fluid (17) can be the fact that it, too, may serve to minimize chemical stresses upon the cells. In one regard, since it may be important to provide a nutrient to the cells both before and after sorting, the collector fluid (17) may be selected so as to provide a coordinated level of nutrient so that the levels are balanced both before and after sorting. For bovine sperm in which a nutrient of egg yolk citrate is utilized at a two percent egg yolk level, it has been discovered that utilizing a six percent egg yolk citrate level (that is six percent egg yolk content in a citrate solution) provides good results. This is as result of the volumes existing before and after the sorting event. The collector fluid (17) may start (before sorting) with about 2 ml of volume. The sorting event may add about double this volume (ending at three times the initial starting volume) with very little egg yolk citrate in solution (due to clogging and other flow cytometer considerations). Thus, the end result in terms of the level of the amount of egg yolk citrate present may be equivalent to the starting result, namely, two percent egg yolk content in a citrate solution due to the volumes involved. Thus the collector fluid (17) may be selected so as to create an ending collector fluid environment which is balanced with the initial nutrient or other fluid environment. In this manner, it may serve to minimize the time and changed level of composition to which the cells are subjected. Naturally, these fluid environments may be presented within the flow cytometer or may exist at some other prior time, the important point being merely minimizing the stress to which the cells are subjected at any time in their life cycle. Furthermore, since the initial chemical substance content can be varied (for instance the percent egg yolk content in the citrate may be varied up or down), likewise the starting collection fluid environment or various volumes may also be varied so that the ending result is the same. Thus, prior to commencing the sorting process, the collector fluid exists with a six percent egg yolk content in the citrate solution and after completion of the sorting event the collector fluid—with the sex-specific sperm—may result in a two percent egg yolk content in the citrate solution similar to the initial nutrient content.

Note that in later use these sperm cells may be treated to a 20% egg yolk content in the citrate fluid for other reasons, however these changes are not deemed to provide stress to the cells as they are merely a known part of the total insemination process. While naturally the levels may be varied as those skilled in the art readily understand, a 20% egg yolk citrate buffer may be constituted as follows:

I. FINAL COMPOSITION:
   80% sodium citrate solution (72 mM)
   20% (vol/vol) egg-yolk
II. PREPARATION FOR 1 LITER:
   A. Sodium citrate solution
      1. Place 29.0 grams of sodium citrate dihydrate ($Na_3C_6H_5O_7 \cdot 2H_2O$) in a 1,000 ml volumetric flask
      2. Add deionized or Nanopure water to make 1,000 ml final volume.
      3. Transfer to bottles and autoclave at 15 lbs pressure (245° F.) for at least 30 minutes.
         a. Autoclave solution using conditions to minimize evaporation (loose cover)
         b. Be careful that water does not boil away.
      4. Cool slowly at room temperature.
      5. Store sealed in a 5° C. cold room.
   B. Egg preparation
      1. Obtain fresh hen's eggs from a good commercial source.
      2. Wash the eggs free of dirt (do not use too much detergent) and rinse.
      3. Immerse eggs in 70% ethanol for 2–5 minutes.
      4. Remove eggs and allow to dry (or wipe dry) and store on a clean towel.
   C. Preparation of extender
      1. Use sterile, clean glassware
      2. A-fraction (non-glycerol fraction)
         a. Place 800 ml of 2.9% sodium citrate solution in a 1,000 ml graduated cylinder.
         b. Antibiotic levels for the non-glycerol containing fraction (A-fraction) of the extender may be as follows:
            I. Tylosin = 100 µg/ml
            ii. Gentamicin = 500 µg/ml
            iii. Linco-spectin = 300/600 µg/ml
         c. Add 200 ml of fresh egg-yolk as outlined below (Section D)

-continued

I. Mix very thoroughly.
      d. This provides A-fraction extender based on 2.9% sodium citrate, with 20% egg-yolk and antibiotics at concentrations known to be non-toxic to bull sperm.
      e. Extender can be stored overnight at 5° C.
      f. Decant supernatant (upper 800 ml) the next day.
      g. Warm to 37° C. prior to use the next day.
   D. To add egg-yolk to a buffered solution, the following procedure works well.
      1. Wash egg and clean the eggs (see B above)
      2. Open egg and separate yolk from albumin using a yolk separator. Alternatively, pour yolk back and forth 2–3 times between the two half shells. Do not rupture the membrane around the yolk.
      3. Place the yolk onto a sterile piece of 15 cm filter paper.
      4. Hold the filter paper over the graduated cylinder containing buffer and squeeze the yolk (rupturing the membrane) and allow the yolk to run out of the golded filter paper into the cylinder. Typically about 12–15 ml of the yolk can be obtained from one egg.

Another aspect which may interplay in the various factors of the present invention is that of utilizing low dose amounts of sperm for artificial insemination or the like. Additional background on the aspect of sexed, artificial insemination may be found in "Prospects for Sorting Mammalian Sperm" by Rupert P. Amman and George E. Seidel, Jr., Colorado Associated University Press (1982) hereby incorporated by reference. As mentioned, natural insemination involves numbers of sperm on the order of billions of sperm. Typical artificial insemination is presently conducted with millions of sperm for bovine species and hundreds of millions of sperm for equine species. By the term "low dose" it is meant that the dosage of sperm utilized in the insemination event are less than one-half or preferably even less than about 10% of the typical number of sperm provided in a typical artificial insemination event. Thus, the term "low dose" is to be viewed in the context of the typical artificial insemination dosage or also as an absolute number. For bovine sperm where currently 1 to 10 million sperm are provided, a low dose process may be considered an absolute number of about 500,000 sperm or perhaps as low as 300,000 sperm or lower. In fact, through utilization of the techniques of the present invention, artificial insemination with good percentages of success has been shown with levels of insemination of sperm at 100,000 and 250,000 sperm (41% and 50%, respectively pregnancy rates). As shown in the article "Uterine Horn Insemination of Heifers With Very Low Numbers of Non-frozen and Sexed Spermatozoa" as published in 48 Theriogenology 1255 (1997) hereby incorporated by reference. Since sperm cells appear to display a sensitivity to dilution, these results may display particular interdependence on the utilization of low dose sperm samples with regards to various techniques of the present invention. The absolute numbers may be species dependent, for equine species, merely less than about ten, five, or even one million sperm may be considered a low dose process.

Another aspect which may be important is the fact that the sperm sexed through the present invention techniques is utilized in an artificial insemination system. Thus, when the collector (14) is used to provide sperm for artificial insemination the techniques of the present invention may be particularly relevant. Further, it is possible that the combination of both artificial insemination use and the use in a low dose environment may together create synergies which makes the various techniques of the present invention particularly appropriate. Naturally, the sexed sperm can be utilized not just in an artificial insemination mode, but in other techniques such as in vitro fertilization and the like.

The process of collecting, sorting, and eventually inseminating an animal through the use of flow cytometry involves a variety of steps. In the context of bovine insemination, first the semen is collected from the bull through the use of an artificial vagina. This occurs at rates of approximately 1.5 billion sperm per ml. This neat semen may be checked through the use of a spectrophotometer to assess concentration and may be microscopically evaluated to assure that it meets appropriate motility and viability standards. Antibiotics may then added. As a result the initial sample may have approximately 60 to 70 percent of the progressively motile sperm per ejaculate. For processing, a dilution through of some type TALP (tyrode albumin lactate pyruvate) may be used to get the numbers of sperm at a manageable level (for flow analysis) of approximately 100 million per ml. The TALP not only nurtures the sperm cells, but it may make them hyper-activated for the staining step. Prior to staining, in some species such as the equine species, centrifugation may be accomplished. Staining may be accomplished according to a multi-stained or single-stained protocol, the latter, the subject of the Johnson Patent and related technology. The staining may be accomplished while also adjusting the extender to create the appropriate nutrient environment. In bovine applications this may involve adding approximately 20% egg yolk content in a citrate solution immediately after staining. Further, in staining the sperm cells, it has been discovered that by using higher amounts of stain than might to some extent be expected better results may be achieved. This high concentration staining may involve using amounts of stain in the tens of micro-molar content such as discussed in the examples below where 38 micro-molar content of Hoechst 33342 stain was used.

After adding the stain, an incubation period may be used such as incubating at one hour at 34° C. to hasten the dye uptake with concentrations at about 100 million sperm cells per ml. Filtration may then be accomplished to remove clumps of sperm cells and then dilution or extending may or may not be accomplished to the desired sort concentration of approximately 100 million sperm cells per ml may be accomplished. Sorting according to the various techniques discussed earlier may then be accomplished from which sperm cells may be recovered in the collection phase. As mentioned earlier, the collection may result in samples with approximately 2% egg yolk citrate concentrate content (for bovine species). This sample may then be concentrated to about 3–5 million sperm cells per ml through the use of centrifugation after which the sheath fluid and preserving fluid may be removed. A final extension may then be accomplished with either 20% egg yolk citrate or a Cornell Universal Extender or the like. The Cornell Universal Extender may have the following composition for 1000 ml:

14.5 g sodium citrate dihydrate
2.1 g $NaHCO_3$
0.4 g KCl
3.0 g glucose
9.37 g glycine
0.87 g citric acid
For 20% egg-yolk using 800 ml of above preparation and may include about 200 ml of egg-yolk composition.

After this last extending, 3 to 5 million sperm per ml (for bovine species) may result. This sample may then be cooled to slow the sperm's metabolism and to permit use over longer periods of time. In the equine species the sample may then be used in oviductal or other insemination processes as those skilled in the art well understand. In bovine sperm, the sample may be diluted yet one more time to the desired dosage level. It has been discovered that dilution may create an effect upon the sperm cell's viability and so it may be appropriate to avoid too large a level of dilution by providing a smaller sample. At present, low dosages of approximately 300,000 sperm per 0.184 ml may be achieved. Furthermore, it may be desirable to maintain a level of seminal plasma at approximately a five percent level, although the results of this requirement are, at present, mixed. The sperm cell specimen may then be placed in a straw for use in artificial insemination and may be transported to the cows or heifers to be inseminated.

In order to achieve conveniently timed artificial insemination, heifer or cow estrus may be synchronized using known techniques such as the utilization of prostaglandin $F2_\alpha$ according to techniques well known in the art. This latter substance may be particularly valuable in that it has been reported to potentially achieve enhanced fertility in heifers as discussed in the article "Prostoglandin $F2_\alpha$—A Fertility Drug in Dairy Cattle?", 18 Theriogenology 245 (1982) hereby incorporated by reference. While recent results have not maintained this premise, it may be that the present invention demonstrates its particular viability in situations of sexed, low dose insemination. For bovine species, artificial insemination may then be accomplished through the use of embryo transfer equipment with placement of the sperm cells deep within the uterine horns. This may be accomplished not at the peak moment as typically used in artificial insemination, but rather at a somewhat later moment such as 12 hours after that time since there is some possibility that fertility for sexed artificial insemination may occur slightly later. The utilization of embryo transfer equipment may be used because there may be high sensitivity of the uterine wall for such low dose, sexed inseminations.

Further the techniques can be combined to achieve higher efficiency production as well. Particularly, the processes now invented which permit high speed sorting and low dose insemination of sexed embryos is also possible in a superovulated animal. The superovulation may be achieved by use of a superovulatory pharmaceutical or by any other technique. The superovulatory pharmaceutical may act directly or indirectly, such as through a sequence of reactions to achieve a greater than normal production of eggs. The combination with superovulation is surprising because superovulation was previously deemed to hinder such a combination. Sperm transport is compromised in superovulated cattle, so, animals were frequently artificially inseminated on multiple occasions and/or with multiple doses of semen. Also, prior procedures for sexing semen were relatively slow; therefore, it was of interest to determine fertilization rates after a single insemination of superovulatory pharmaceutical, such as FSH (follicle stimulating hormone)—treated cattle with only 600,000 total sexed unfrozen sperm using these newer combination of techniques.

By example, twelve Angus crossbred heifers were superovulated using standard procedures: 6, 6, 4, 4, 2, 2, 2, and 2 mg FSH were injected intramuscularly at half-day intervals beginning between days 9 and 12 of the estrous cycle; 25 and 12.5 mg prostaglandin F-2 alpha were injected intramuscularly with the 6th and 7th FSH injections. Sperm from bulls of unknown fertility were stained with Hoechst 33342 and then sorted using a MoFlo® flow cytometer/cell sorter yielding 700–800 live sperm of each sex/sec. Average sort purity was 89% of the desired sex. Sorted sperm were concentrated to $3.36 \times 10^6$ sperm/ml by centrifugation at 650 g for 10 min, cooled to 5° C., and stored 4 h. Then 184 ul were loaded in 0.25 ml plastic straws; half the dose was inseminated into each uterine horn 20 to 24 h post-onset of estrus using automatic side-opening embryo transfer sheaths. Embryos were collected by standard non-surgical procedures at 7 or 16 days post-estrus. Results were similar between day 7 and 16 collections and between X- and Y-sorted sperm. Embryos were recovered from 9 heifers. There were 52 embryos (mean, 4.3±5.3/donor) at normal stages of development, 13 retarded embryos and 31 unfertilized ova. Forty-six embryos were sexed by PCR using primers for a Y-chromosome-specific DNA sequence; 43 (93%) were of the intended sex. Although this study involved few animals, surprisingly, insemination of superovulated heifers with only 600,000 total (live) sexed unfrozen sperm gave similar results to conventional procedures. Variations on the above may also be accomplished, including, but not limited to, sorting through other than flow cytometric means, achieving superovulation in other manners, increasing fertility in other manners, and the like.

Further, the congruence of methods of sexing sperm based on DNA content, high speed flow cytometer/cell sorters, and procedures for inseminating heifers with fewer than 500,000 total sperm without compromising fertility has resulted in the possibility of a viable sexed semen industry in cattle within a few years. There will be a myriad of applications for sperm sexed at <85% accuracy. Perhaps the most obvious is inseminating one subset of cattle (both dairy and beef) for female herd replacements, and having the converse subset (both dairy and beef) bred to entirely different types of bulls to produced males for meat. A very important subset of the above is inseminating heifers with X-chromosome-bearing sperm to produce female calves, which have a lower incidence of dystocia than male calves, primarily due to smaller size. Furthermore, proving young dairy sires would be much more efficient with a preponderance of heifer calves. Having more than 85% heifer calves also makes it feasible to manage dairy cows so they average fewer than two surviving calves per lifetime, which is attractive because of reducing problems associated with gestation and parturition. Single sex systems of beef production also would become feasible, in which each female replaces herself and is slaughtered between 2 and 3 years of age, thus using a much higher percentage of nutrients in the system for growth, and a lower percentage for maintenance. Sexed semen would be useful for in vitro fertilization and to inseminate cows superovulated for embryo transfer. Frequently one sex of calves is considerably more valuable than the other, and although accurate methods of sexing embryos are available, they are time-consuming, and half of the embryos produced are of the less valuable sex. it is surmised that accurately sexed semen would be widely adopted for artificial insemination of cattle if the sexing surcharge were low and fertility was only minimally compromised. The percentage of beef cattle inseminated artificially likely would increase substantially with sexed semen.

Interestingly, rather than inseminating within the uterine body where such insemination are usually placed, by insemination deep within the uterine horn, better results may be achieved. Perhaps it is also surprising that the samples thus far studied have shown no difference between ipsi- and contra-lateral inseminations when accomplished deep within the uterine horn. By deep, it should be understood that the insertion is placed well into the uterine horn using the embryo transfer equipment. The fact that results do not appear significantly different using ipsi- and contra-lateral inseminations has led the present inventors to propose the use of insemination in both so that the process of identifying the appropriate uterine horn may no longer be needed.

As a result of the insemination, it is of course desired that an animal of the desired sex be produced. This animal may be produced according to the systems discussed earlier through the use of the sexed sperm specimen. It should also be understood that the techniques of the present invention may find application in other techniques such as laproscopic insemination, oviductal insemination, or the like.

As examples, the following experiments have been conducted. While not all use every aspect of the inventions described here, they do show the performance enhancements possible through differing aspects of the invention. Further, a summary of some experiments is contained in the article "Uterine Horn Insemination of Heifers With Very Low Numbers of Non-frozen and Sexed Spermatozoa" as referenced earlier. This article summarizes some of the data showing the efficacy of the present invention. As to the experiments, one has been conducted with sexed, unfrozen sperm cells with high success as follows:

EXAMPLE 1

Angus heifers, 13–14 mo of age and in moderate body condition, were synchronized with 25 mg of prostaglandin F-2 alpha at 12-day intervals and inseminated 6–26 h after observed standing estrus. Freshly collected semen from three 14–26 mo old bulls was incubated in 38 $\mu$M Hoechst 33342 at $75 \times 10^6$ sperm/ml in a TALP medium for 1 h at 34° C. Sperm were sorted by sex chromosomes on the basis of epiflourescence from laser excitation at 351 and 364 nm at 150 mW using a MoFlo® flow cytometer/cell sorter operating at 50 psi and using 2.9% Na citrate as sheath fluid. X chromosome-bearing sperm (~90% purity as verified by resorting sonicated sperm aliquots) were collected at ~500 live sperm/sec into 2-ml Eppendorf tubes containing 100 $\mu$l Cornell Universal Extender (CUE) with 20% egg yolk. Collected sperm were centrifuged at 600×g for 10 min and resuspended to $1.63 \times 10^6$ live sperm/ml in CUE. For a liquid semen unsexed control; Hoechst 33342-stained sperm were diluted with sheath fluid to $9 \times 10^5$ sperm/ml and centrifuged and resuspended to $1.63 \times 10^6$ progressively motile sperm/ml in CUE. Sexed semen and liquid control semen were cooled to 5° C. over 75 min and loaded into 0.25-ml straws (184 ul/straw). Straws were transported at 3 to 5° C. in a temperature-controlled beverage cooler 240 km for insemination 5 to 9 h after sorting. Sexed semen and liquid control semen were inseminated using side-opening blue sheaths (IMV), one half of each straw into each uterine horn ($3 \times 10^5$ live sperm/heifer). As a standard control, semen from the same bulls had been frozen in 0.5-cc straws by standard procedures (mean $15.6 \times 10^6$ motile sperm/dose post-thaw), thawed at 35° C. for 30 sec, and inseminated into the uterine body. Treatments were balanced over the 3 bulls and 2 inseminators in a ratio of 3:2:2 inseminations for the sexed semen and two controls. Pregnancy was determined ultrasonically 31–34 days after insemination and confirmed 64–67 days later when fetuses also were sexed (blindly). Data are presented in the table.

| Treatment | No. Heifers bred | No. Pregnant d31–34 | No. Pregnant d64–67 | No female fetuses |
| --- | --- | --- | --- | --- |
| Sexed semen | 45 | 20 (44%) | 19 (42%) | 18 (95%)[a] |
| Liquid control | 28 | 15 (54%) | 15 (54%) | 8 (53%)[b] |
| Frozen control | 29 | 16 (55%) | 15 (52%) | 12 (80%)[c] |

[a,b]Sex ratios of values with different superscripts differ (P < 0.02).

Although the pregnancy rate with sexed semen was only 80% of controls, this difference was not statistically significant (>0.1). One pregnancy was lost by 64–67 d in each of the sexed and frozen control groups; 18 of 19 fetuses (95%) were female in the sexed group, and 20 of 30 (67%) were female in the control groups. The liquid semen control yielded a virtually identical pregnancy rate to the frozen semen control containing over 50 times more motile sperm (over 120 times more total sperm), demonstrating the efficacy of low-dose insemination into the uterine horns. We have altered the sex ratio in cattle significantly using flow cytometer technology and artificial insemination.

Similarly, an experiment was conducted with unsexed, unfrozen sperm cells and may be reported as follows:

EXAMPLE 2

The objective was to determine pregnancy rates when heifers are inseminated with extremely low numbers of frozen sperm under ideal field conditions. Semen from three Holstein bulls of above average fertility was extended in homogenized milk, 7% glycerol (CSS) extender plus 5% homologous seminal plasma to $2 \times 10^5$, $5 \times 10^5$ or $10 \times 10^6$ (control) total sperm per 0.25 ml French straw and frozen in moving liquid nitrogen vapor. Semen was thawed in 37° C. water for 20 sec. Holstein heifers 13–15 mo of age weighing 350–450 kg were injected with 25 mg prostaglandin F-2-alpha (Lutalyse®) twice at a 12-day interval and inseminated with an embryo transfer straw gun and side-opening sheath, half of the semen deep into each uterine horn 12 or 24 h after detection of estrus. The experiment was done in five replicates over 5 months, and balanced over two insemination technicians. Ambient temperature at breeding was frequently −10 to −20° C., so care was taken to keep insemination equipment warm. Pregnancy was determined by detection of a viable fetus using ultrasound 40–44 days post-estrus and confirmed 55–62 days post-estrus; 4 of 202 conceptuses were lost between these times. Day 55–62 pregnancy rates were 55/103 (53%), 71/101, (70%), and 72/102 (71%) for $2 \times 10^5$, $5 \times 10^5$ and $10 \times 10^6$ total sperm/inseminate (P<0.1). Pregnancy rates were different (P<0.05) among bulls (59, 62, and 74%), but not between technicians (64 and 65%) or inseminations times post-estrus (65% for 12 h and 64% for 24 h, N=153 at each time). With the methods described, pregnancy rates in heifers were similar with $5 \times 10^5$ and $10 \times 10^6$ total sperm per inseminate.

Prior a experiment has also been conducted on sexed, unfrozen sperm cells and may be reported as follows:

EXAMPLE 3

Semen was collected from bulls at Atlantic Breeders Cooperative, diluted 1:4 with a HEPES-buffered extender +0.1% BSA, and transported 160 km (~2 HR) to Beltsville, Md. where it was sorted at ambient temperature by flow cytometry into a TEST yield (20%) extender using methods described previously (Biol Reprod 41:199). Sorting rates of up to $2 \times 10^6$ sperm of each sex per 5–6 h at ~90% purity were achieved. Sperm were concentrated by centrifugation (300 g for 4 min) to $2 \times 10^6$ sperm/ml. Some sperm were sorted into extender containing homologous seminal plasma (final concentration, 5%). Sorted sperm were shipped by air to Colorado (~2,600 km) and stored at either ambient temperature or 5° C. (cooled during shipping over 6 hr in an Equitainer, an insulated device with an ice-containing compartment). Heifers or dry cows detected in estrus 11 to 36 h earlier were inseminated within 9 to 29 h of the end of the sperm sorting session. Sperm (1 to $2 \times 10^5$ in 0.1 ml) were deposited deep in the uterine horn ipsilateral to the ovary with the largest follicle as determined by ultrasound at the time of insemination.

None of 10 females became pregnant when inseminated with sperm shipped and stored at ambient temperature. Of 29 females inseminated with sperm cooled to 5° C. during shipping, 14 were pregnant at 4 weeks of gestation, and 12 (41%) at 8 weeks. Eleven of the 22 inseminated within 10 h of the end of sorting were pregnant at 8 weeks, but only 1 of 7 inseminated 17–24 h after sorting was pregnant. There was no significant effect of adding seminal plasma. One of the 12 fetuses was not of the predicted sex, one was unclear, and 10 were of the predicted sex, as determined by ultra-sonography at 60–70 days of gestation.

Subsequently, 33 additional heifers were inseminated with 0.05 ml (semen extended as described above) into each uterine horn without using ultrasonography; only 3 were pregnant 4 weeks after insemination, and only 1 remained pregnant at 8 weeks. However, different bulls were used from the previous group, and all inseminations were done 18–29 h post-sorting. An additional 38 heifers were inseminated similarly (~22 h post-sorting) 200 km from our laboratory with sorted sperm from another bull; none of these was pregnant 8 weeks after insemination.

To summarize, it is possible to achieve pregnancies in cattle via artificial insemination of sperm sorted for sex chromosomes by flow cytometry, and the sex ratio of fetuses approximates that predicted by reanalysis of sorted sperm for DNA content (90%). However, pregnancy rates varied greatly in these preliminary experiments which required shipping sperm long distances. Fertility decreased drastically by 17 h post-sorting, but there was some confounding because different bulls were used at the different times. Further studies are needed to determine whether variation observed in pregnancy rates was due to bull differences, insemination techniques, interval between sorting and insemination, or other factors.

Finally, an experiment also has been conducted with unsexed, unfrozen sperm cells and may be reported as follows:

EXAMPLE 4

The objective was to determine pregnancy rates when heifers were inseminated with very low numbers of sperm under ideal experimental conditions. Semen from three Holstein bulls was extended in Cornell Universal Extender plus 5% homologous seminal plasma to $1 \times 10^5$ or $2.5 \times 10^5$ sperm per 0.1 ml; $2.5 \times 10^6$ total sperm per 0.25 ml was used as a control. Fully extended semen was packaged in modified 0.25 ml plastic French straws to deliver the 0.1 or 0.25 ml inseminate doses. Semen was cooled to 5° C. and used 26–57 h after collection. Holstein heifers 13–15 mo of age weighing 350–450 kg were injected with 25 mg prostaglandin F-2 alpha (Lutalyse®) at 12-day intervals and inseminated with an embryo transfer straw gun and side-opening sheath into one uterine horn 24 h after detection of estrus. Insemination was ipsilateral to the side with the largest follicle determined by ultrasound 12 h after estrus; side of ovulation was verified by detection of a corpus luteum by ultrasound 7–9 days post-estrus. Pregnancy was determined by detection of a fetus by ultrasound 42–45 days post estrus. The experiment was done in four replicates and balanced over three insemination technicians. Side of ovulation was determined correctly in 205 of 225 heifers (91%); surprisingly, pregnancy rates were nearly identical for ipsilateral and contralateral inseminates. Pregnancy rates were 38/93 (41%), 45/87 (52%), and 25/45 (56%) for $1\times10^5$, $2.5\times10^5$ and $2.5\times10^6$ sperm/inseminate (P>0.1). There was a significant difference in pregnancy rate (P<0.05) among technician, but not among bulls. With the methods described, it may be possible to reduce sperm numbers per inseminate sufficiently that sperm sorted by sex with a flow cytometer would have commercial application.

As mentioned and as can be seen from the various experiments, the field is statistically based and thus a variety of additional experiments may be conducted to show the appropriate combination and limitation strategies. Thus synergies among various affects will further be identified, such as instances in which the dye effects and combined dye effects with laser excitation may be studied.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which may be submitted. It should be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. As but one example of this aspect, the disclosure of a "collector" should be understood to encompass disclosure of the act of "collecting"—whether explicitly discussed or not—and, conversely, were there only disclosure of the act of "collecting", such a disclosure should be understood to encompass disclosure of a "collector." Such changes and alternative terms are to be understood to be explicitly included in the description.

Any references mentioned in the application for this patent as well as all references listed in any information disclosure filed with the application are hereby incorporated by reference; however, to the extent statements might be considered inconsistent with the patenting of this/these invention(s) such statements are expressly not to be considered as made by the applicant(s).

We claim:

1. A method of producing multiple, sexed embryos from a female mammal comprising:
    a. creating superovulation in said female mammal to create at least two eggs comprising the step of using an ovulatory pharmaceutical to cause multiple eggs to be produced comprising the steps of:
        i) injecting a dosage of follicle stimulating hormone a plurality of times a day;
        ii) administering said dosage of follicle stimulating hormone with prostaglandin F-2-alpha;
        and wherein said step of injecting said dosage of follicle stimulating hormone a plurality of times a day comprises injecting said follicle stimulating hormone in approximately half day increments at a dosage level of 6, 6, 4, 4, 2, 2, 2, and 2 mg between days 9 and 12 inclusive of the estrus cycle and wherein administering said dosage of follicle stimulating hormone with prostaglandin F-2-alpha comprises supplementing 25 and 12.5 mg of prostaglandin F-2-alpha on the sixth and seventh dosages, respectively, of said follicle stimulating hormone;
    b. determining a sex of a sperm cell of a male mammal;
    c. sorting according to said sex of said sperm cells;
    d. inserting at least a portion of said sorted sperm cells into a uterus of said female mammal after an onset of estrus; and
    e. fertilizing a plurality of said eggs to produce at least two sexed embryos of the desired sex from said female mammal.

2. A method of producing multiple, sexed embryos according to claim 1 wherein said step of using a an ovulatory pharmaceutical comprises the step of injecting said ovulatory pharmaceutical in half days increments between any of days 2 and 18 of said estrus cycle.

3. A method of producing multiple, sexed embryos as described in claim 2 wherein injecting said ovulatory pharmaceutical in half day increments comprises injecting at least seven injections and further comprising the step of incorporating an estrus manipulation system at least on about the sixth and seventh injections.

4. A method of producing multiple, sexed embryos as described in claim 3 wherein inserting at least a portion of said sorted sperm cells into said uterus comprises inserting said sperm cells into both uterine horns of said uterus.

5. A method of producing multiple, sexed embryos as described in claim 4 wherein inserting into both uterine horns comprises inserting said sperm cells approximately between 20 to 24 hours inclusive after said onset of said estrus.

6. A method of producing multiple, sexed embryos as described in claim 1 and further comprising the steps of:
   a. staining sperm cells of a male mammal;
   b. sorting according to said sex of said sperm cells at sperm cell sorting rates above 500 sorts per second; and
   c. concentrating said sorted sperm cells.

7. A method of producing multiple, sexed embryos as described in claim 1 wherein inserting at least a portion of said sorted sperm cells comprises using a low dose of said sperm cells.

8. A method of producing multiple, sexed embryos as described in claim 6 wherein inserting at least a portion of said sorted sperm cells comprises using a low dose of said sperm cells.

9. A method of producing a mammal of a desired sex comprising producing said mammal using the processes as described in claims 1.

10. A method of producing a mammal of a desired sex comprising producing a sexed sperm cells mammal using the processes of claim 9 further comprising sorting said cells at sperm cell sorting rates above 500 sorts per second.

11. A method of producing a mammal of a desired sex as described in claim 9 further comprising inseminating a female mammal using a low dose of said sperm cells to produce said mammal of a desired sex.

12. A method of producing multiple, sexed embryos comprising the steps of:
   a. creating superovulation in a female mammal to create at least two eggs using an ovulatory pharmaceutical to cause multiple eggs to be produced;
   b. chemically coordinating a sheath fluid to create a sheath fluid environment for sperm cells of a male mammal which is coordinated with both a pre-sort and a post-sort cell fluid environment comprising establishing a sheath fluid which contains about 2.9% sodium citrate;
   c. determining a sex of said sperm cells;
   d. sorting according to said sex of said sperm cells;
   e. inserting at least a portion of said sorted sperm cells into a uterus of said female mammal after an onset of estrus; and
   f. fertilizing a plurality of said eggs to produce at least two sexed embryos of the desired sex from said female mammal.

13. A method of producing multiple, sexed embryos as described in claim 12 wherein chemically coordinating a sheath fluid to create a sheath fluid environment for said cells which is coordinated with both a pre-sort and a post-sort cell fluid environment comprises establishing a sheath fluid which contains a HEPES buffered medium.

14. A method of producing multiple, sexed embryos as described in claim 13 further comprising collecting cells of said desired sex and cushioning said cells from impact with a collection container which has a wide opening.

15. A method of producing multiple, sexed embryos as described in claim 12 and further comprising the steps of:
   a. staining sperm cells of a male mammal;
   b. sorting according to said sex of said sperm cells at sperm cell sorting rates above 500 sorts per second; and
   c. concentrating said sorted sperm cells.

16. A method of producing multiple, sexed embryos as described in claim 12 wherein inserting at least a portion of said sorted sperm cells comprises using a low dose of said sperm cells.

17. A method of producing multiple, sexed embryos as described in claim 15 wherein inserting at least a portion of said sorted sperm cells comprises using a low dose of said sperm cells.

18. A method of producing a mammal of a desired sex comprising producing said mammal using the processes as described in claim 12.

19. A method of producing a mammal of a desired sex comprising producing said mammal using the processes as described in claim 13.

20. A method of producing a mammal of a desired sex comprising producing said mammal using the processes as described in claim 16.

* * * * *

UNITED STATES PATENT AND TRADEMARK OFFICE
CERTIFICATE OF CORRECTION

PATENT NO.   : 6,071,689
DATED        : June 6, 2000
INVENTOR(S)  : George Seidel, Lisa Herickhoff and John Schenk It is certified that error appears in the above-identified patent and that said Letters Patent is hereby corrected as shown below:

<u>Title page,</u>
Item [73], should read -- Assignee: Colorado State University through its agent Colorado State University Research Foundation and XY, Inc., Fort Collins, Colo --

Signed and Sealed this

Thirty-first Day of December, 2002

JAMES E. ROGAN
*Director of the United States Patent and Trademark Office*

UNITED STATES PATENT AND TRADEMARK OFFICE
CERTIFICATE OF CORRECTION

Page 1 of 1

PATENT NO.        : 6,071,689
APPLICATION NO.   : 09/015454
DATED             : June 6, 2000
INVENTOR(S)       : George Seidel et al.

It is certified that error appears in the above-identified patent and that said Letters Patent is hereby corrected as shown below:

In the Claims

Col. 22, Line 36, Claim 19 should read

19. A method of producing a mammal of a desired sex comprising producing said mammal using the processes as described in claim 15.

Signed and Sealed this
Fifteenth Day of March, 2016

Michelle K. Lee
*Director of the United States Patent and Trademark Office*